(12) United States Patent
Van Den Brink (10) Patent No.: US 10,649,045 B2
(45) Date of Patent: May 12, 2020

(54) SAFETY MONITORING FOR MAGNETIC RESONANCE IMAGING

(71) Applicant: KONINKLIJKE PHILIPS N.V., Eindhoven (NL)

(72) Inventor: Johan Samuel Van Den Brink, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 399 days.

(21) Appl. No.: 15/030,629

(22) PCT Filed: Oct. 9, 2014

(86) PCT No.: PCT/EP2014/071643
§ 371 (c)(1),
(2) Date: Apr. 20, 2016

(87) PCT Pub. No.: WO2015/058966
PCT Pub. Date: Apr. 30, 2015

(65) Prior Publication Data
US 2016/0252592 A1    Sep. 1, 2016

(30) Foreign Application Priority Data

Oct. 21, 2013  (EP) ...................................  13189500

(51) Int. Cl.
*G01R 33/28* (2006.01)
*A61B 5/05* (2006.01)
(Continued)

(52) U.S. Cl.
CPC .............. *G01R 33/288* (2013.01); *A61B 5/05* (2013.01); *A61B 5/063* (2013.01); *A61B 5/055* (2013.01)

(58) Field of Classification Search
None
See application file for complete search history.

(56) References Cited

U.S. PATENT DOCUMENTS 4,690,149 A    9/1987   Ko
4,712,068 A *  12/1987  Savelainen ...... G01R 33/34046
                                                 324/318
(Continued)

FOREIGN PATENT DOCUMENTS

JP    2008017989 A    1/2008
WO    2007017779 A2   2/2007
(Continued)

OTHER PUBLICATIONS

Finn et al "Ferromagnetic Materials in Patients: Detection Before MR Imaging" Radiology: Radiological Society of North America vol. 156, No. 1 Jul. 1985 p. 139-141.
(Continued)

*Primary Examiner* — Paresh Patel (57) ABSTRACT

The present invention provides a safety monitoring device (10) for detecting radio frequency resonances in a subject of interest (12) comprising an essentially tubular examination space (14), which is vertically arranged, for locating therein the subject of interest (12), an radio frequency resonance device (16), which has at least one connection port (21), for covering at least a part of the examination space (14) along its longitudinal axis, a rotation device (22) for rotating the radio frequency resonance device (16) relative to the subject of interest (12), a controlling device (30) for controlling the rotation of the radio frequency resonance device (16), and a detection device (34) for monitoring an impedance of the at least one connection port (21) of the radio frequency resonance device (16) during the rotation and detecting radio frequency resonances out of the monitored impedance of the at least one connection port (21) of the radio frequency resonance device (16). The present invention further provides a method for detecting radio frequency resonances in a subject of interest (12) comprising the steps of locating the subject of interest (12) within an essentially tubular exami- (Continued)

nation space (14), which is vertically arranged, rotating a radio frequency resonance device (16), which has at least one connection port (21), relative to at least a part of the examination space (14) along its longitudinal axis, monitoring an impedance of the at least one connection port (21) of the radio frequency resonance device during (16) the rotation, and detecting radio frequency resonances out of the monitored impedance of the at least one connection port (21) of the radio frequency resonance device (16).

20 Claims, 3 Drawing Sheets (51) Int. Cl.
*A61B 5/06* (2006.01)
*A61B 5/055* (2006.01)

(56) References Cited

U.S. PATENT DOCUMENTS

| | | | | |
|---|---|---|---|---|
| 4,820,983 | A * | 4/1989 | Bendall | G01R 33/446 324/307 |
| 6,806,713 | B2 * | 10/2004 | Wong | G01R 33/34053 324/307 |
| 2005/0225327 | A1 | 10/2005 | Maschke | |
| 2006/0125475 | A1 | 6/2006 | Sodickson et al. | |
| 2008/0275333 | A1 * | 11/2008 | Fain | A61B 5/055 600/422 |
| 2011/0160565 | A1 | 6/2011 | Stubbs et al. | |
| 2011/0210735 | A1 | 9/2011 | Trakic et al. | |
| 2011/0248727 | A1 * | 10/2011 | Krumme | H02J 50/12 324/652 |
| 2012/0112748 | A1 * | 5/2012 | Hetherington | G01R 33/34007 324/318 |
| 2015/0253393 | A1 * | 9/2015 | Harvey | G01R 33/34076 324/322 |

FOREIGN PATENT DOCUMENTS

| | | |
|---|---|---|
| WO | 2007124273 A1 | 11/2007 |
| WO | 2010113121 A1 | 10/2010 |
| WO | 20100126935 A2 | 11/2010 |
| WO | 2013001292 A2 | 1/2013 |

OTHER PUBLICATIONS

Ellenor et al "A Low Power Offline Prescreen to Detect and Suppress Dangerous Currents", Proc. Intl. Soc. Mag. Reson. Med 21 (2013) p. 4411.

Graesslin et al "Detection of RF Unsafe Devices Using a Parallel Transmission MR System", Magnetic Resonance in Medicine (2012).

* cited by examiner

SAFETY MONITORING FOR MAGNETIC RESONANCE IMAGING

CROSS REFERENCE TO RELATED APPLICATIONS

This application is a U.S. national phase application of International Application No. PCT/EP2014/071643, filed on Oct. 9, 2014, which claims the benefit of EP Application Serial No. 13189500.5 filed on Oct. 9, 2013 and is incorporated herein by reference.

FIELD OF THE INVENTION

The invention relates to the field of magnetic resonance imaging and in particular to safety monitoring for magnetic resonance imaging.

BACKGROUND OF THE INVENTION

The invention relates to a safety monitoring device to be located at the entrance of a magnetic resonance (MR) examination room. The safety monitoring device assesses whether it is safe for the subject of interest, i.e. a patient, to undergo a MR examination in a MR examination room, notably in a electro-magnetic field region of a MR examination system located within the MR examination room.

State of the art in safety for performing examinations using an MR examination system is an interview with the patient prior to the examination to identify if the patient is free of components which might cause problems during the examination or which might cause harm to the patient. Hence, the safety of the MR examination depends on the information provided by the patient, and this method has a low reliability.

To improve safety, it is known e.g. from WO 2013/001292 A2 to use an apparatus for detecting ferromagnetic objects located on or in a patient, who is to be examined subsequently using a MR examination device. The apparatus comprises a magnetic sensor, which in use measures an ambient magnetic field or gradient within an examination space, and a warning device. Accordingly, ferromagnetic objects a patient may inadvertently be carrying are detected and a respective warning is generated. Such objects may cause degradation in the MRI image and require the patient to be re-scanned. Examples of objects in this category include hair/bobby pins, wrist-watches and jewelry clasps and pins.

Magnetic materials are not the sole reason of concern in MR imaging. Also resonant radio frequency (RF) structures can lead to potentially unsafe situations. Such structures can be stents, passive implants, or leads for active implants. None of these are typically ferromagnetic, and will go undetected by the above apparatus. Nevertheless, these structures can be stimulated by the RF fields applied during MR examination, which may cause harm to the subject of interest. Also imaging quality of the MR examination may suffer from the presence of resonant RF structures. Presence of such resonant RF structures could be detected when the subject of interest is already located inside the examination space of the MR system. Nevertheless, if a resonant RF structure is detected only at that time, the scan strategy must be adapted, or the patient has to be removed and MR scanning cannot be completed. At least, the cause of the RF interference must be identified, and potential MR conditions have to be retrieved, e.g. from an implant database in case the RF resonance is caused by an implant. This reduces the efficiency of the MRI scanning process and the entire department workflow for MR scanning.

MR examination systems are usually very cost intensive. Therefore, it is desired to handle safety questions separate from the MR examination systems to avoid halts of the MR examination system and to improve a workflow which enables a continuous operation of the MR examination system.

SUMMARY OF THE INVENTION

It is an object of the invention to provide a safety monitoring device and method for detecting radio frequency resonances in a subject of interest, which enable an efficient, simple, and reliable detection of the presence of RF resonant structures in the subject of interest that might cause dangerous situations during MR imaging, which avoid undesired halts of the MR examination system.

This object is achieved by a safety monitoring device for detecting radio frequency resonances in a subject of interest comprising an essentially tubular examination space, for locating therein the subject of interest, an radio frequency resonance device, which has at least one connection port, for covering at least a part of the examination space along its longitudinal axis, a rotation device for rotating the radio frequency resonance device relative to the subject of interest, a controlling device for controlling the rotation of the radio frequency resonance device, and a detection device for monitoring an impedance of the at least one connection port of the radio frequency resonance device during the rotation and detecting radio frequency resonances out of the monitored impedance of the at least one connection port of the radio frequency resonance device.

This object is also achieved by a method for detecting radio frequency resonances in a subject of interest comprising the steps of locating the subject of interest within an essentially tubular examination space, which is e.g. vertically arranged, rotating a radio frequency resonance device, which has at least one connection port, relative to at least a part of the examination space along its longitudinal axis, and monitoring an impedance of the at least one connection port of the radio frequency resonance device during the rotation, and detecting radio frequency resonances out of the monitored impedance of the at least one connection port of the radio frequency resonance device.

Accordingly, the subject of interest, i.e. the patient can be easily screened for RF resonances, which may indicate possible risks when performing a MR examination with the monitored subject of interest. With the rotation of the radio frequency resonance device relative to the examination space, the RF resonances can be reliably and reproducibly monitored. Since the safety monitoring device can be operated independently from the MR examination system, it can be located outside a MR examination room. Hence, the monitoring can be performed prior to the examination to enable an efficient workflow. The tubular examination space may be vertically arranged, so that a person, notably a patient and/or accompanying staff can be screened for RF resonances in a standing upright position. In an alternative set of the tubular examination space may be horizontally arranged so that a patient may be screened for RF resonance while lying on a patient bed or patient carrier.

The radio frequency resonance device is adapted to receive RF signals in a frequency range, which corresponds to an operation frequency of a MR examination system. The detection of the RF resonances can be performed in a relatively narrow frequency band, which is adapted to the frequency of the MR examination system to be used subsequent to the safety monitoring. Known MR examination systems may use different frequencies depending on the manufacturer and the used strength of the static magnetic field. Typical values of the strength of the magnetic field are 1 T, 1.5 T, 3 T or 7 T. Preferably, the detection device is tuned to the frequency of the MR examination system. Still further preferred the detection device is adaptable in the selected frequency for detecting the RF resonances of the subject of interest. In particular, the detection device can be set to a center frequency which corresponds with the frequency of the MR examination system. Accordingly, only a relatively narrow frequency band has to be monitored for RF resonances. Alternatively, also broadband implementations of the safety monitoring device can be provided. Broadband refers to the coverage of a frequency range of state of the art MR examination systems of current manufacturers, e.g. system having static magnetic fields of 1 T, 1.5 T, 3 T or 7 T.

Preferably, RF resonances are evaluated from reflection coefficients expressed as S11 or S12 parameters. The reflection parameters can be used for determining the impedance of the radio frequency resonance device.

Preferably, the detection of the RF resonances out of the monitored impedance comprises comparing the monitored impedance to a calibrated response for the subject of interest, i.e. a reference patient having no elements which cause RF resonances. The reference values are preferably provided for different kinds of subjects of interest depending on their typical responses, i.e. patient having a different height, weight and/or characteristic anatomy. Preferably, the safety monitoring device comprises data obtained for a set of reference patients, which are stored in a storage unit of the device. Further preferred, the reference values are stored in the detection device itself, i.e. the detection device comprises the storage unit. Still further preferred, the safety monitoring device comprises a user interface, preferably a graphical user interface, to select the reference values depending on the applicable reference patient depending on above characteristics including gender, height and/or weight.

Preferably, safety monitoring device further comprises means for determining body characteristics of the subject of interest. Further preferred, the safety monitoring device is adapted to automatically select a reference patient based on the determined characteristics of the subject of interest. Alternatively, the safety monitoring device can propose at least one reference patient, which can be selected by an operator of the safety monitoring device. The means for determining characteristics of the subject of interest may comprise scales, height measurement system or an optical scanning device for determining a body structure of the subject of interest. Further preferred, the safety monitoring device comprises a stand for the subject of interest, which comprises scales, so that no additional preparation step is required for monitoring RF resonances of the subject of interest.

Still further preferred, the safety monitoring device comprises an interface for connection to an MR examination system, whereby the interface is adapted to provide body characteristics of the subject of interest to a MR examination system. In a particular embodiment, this interface is provided by the Radiology Information System (RIS), to store safety monitoring results and body characteristics. The body characteristics of the subject of interest can be either determined directly by the safety monitoring device, i.e. when the safety monitoring device comprises means for determining body characteristics of the subject of interest, or based on a selected reference patient. E.g. weight and height can be used in a MR examination system for other safety related provisions. Accordingly, the safety monitoring device can comprise a scales and/or a height measurement device for determining body characteristics.

Preferably, the safety monitoring device further comprises a control unit for controlling the operation of all components of the safety monitoring device. The control unit can be part of e.g. the controlling device or the detection device and does not need to be an individual device. The control unit may comprise a processor and a software executed on the processor, whereby the software when executed performs the control of the operation of all components of the safety monitoring device.

According to a preferred embodiment the safety monitoring device further comprises a ferromagnetic detection device to detect the presence of ferromagnetic objects. Monitoring for ferromagnetic objects together with monitoring objects causing RF resonances in the subject of interest provides a high safety for subsequent MR examination. Furthermore, the image quality obtained by using the MR examination system can be improved and the safety of the patient can be increased. Preferably, the safety monitoring device has a common detection device for detecting radio frequency resonances out of the monitored impedance and for detecting ferromagnetic objects.

According to a preferred embodiment the ferromagnetic detection device is mounted to the radio frequency resonance device. With the radio frequency resonance device being rotatable in respect to the subject of interest, the rotation is also applied to the ferromagnetic detection device. A turning movement performed by the subject of the interest has a low accuracy, so that the detection of ferromagnetic objects is rather difficult. With the ferromagnetic detection device mounted to the radio frequency resonance device, the rotation is performed automatically without providing additional apparatus, and a high accuracy in the detection of ferromagnetic objects at or in the subject of interest can be achieved.

According to a preferred embodiment the rotation device is provided as a rotational stand for the subject of interest. The relative rotation between the subject of interest and the radio frequency resonance device is achieved by a mere rotation of the subject of interest, which is located on the stand. The stand is typically placed on a floor, and is provided so that a patient can easily step thereon. In order to avoid the step, the stand can be integrated into the floor, which facilitates the monitoring for patients being physically handicapped, in particular being handicapped in the legs and/or feet. The patient only has to stand on the stand without moving himself and can be easily monitored.

According to a preferred embodiment the rotation device is provided as a rotational support for the radio frequency resonance device. Since the subject of interest is not moved, i.e. the patient is not rotated, the patient only has to stand for the safety monitoring. Effects of a rotation involving equilibrium problems are avoided. The rotation device can be mounted on the floor and/or the ceiling of the location where the monitoring device is located. In case of mounting the rotation device on the floor, it is preferred that the rotation device is integrated into the floor to facilitate access to the examination space and to reduce barriers.

According to a preferred embodiment the radio frequency resonance device is provided as a tubular coil. Coils of this kind are e.g. from MR examination systems. Typical coils are provided as birdcage coils or volume TEM coils. These coils have an essentially circular cross-section and a tubular shape. The longitudinal extension of such coils known from MR examination systems is approximately 50-60 cm. Nevertheless, since the magnetic and the RF field of the MR examination system are also present outside the coil, in a preferred embodiment the coil is provided with a longitudinal extension being longer than the length of a typical coil used in MR examination systems. Further preferred, the coil has a length for covering essentially the entire examination space.

According to a preferred embodiment the radio frequency resonance device comprises at least one single element resonant structure. The single element resonant structure is preferably a dipole or a TEM element. The single resonant elements can be easily provided at an outer circumference of the examination space and perform a rotational movement relative thereto. The single element resonant structure can have the shape of a bar extending in a e.g. vertical direction. The one or more bars leave the examination space open which facilitates access. Since no closed tubular structure is used, such radio frequency resonance devices are suitable in case a patient suffers from claustrophobia.

According to a preferred embodiment the radio frequency resonance device is displaceable in the vertical direction between an operating position, in which the radio frequency resonance device is provided for covering at least a part of the examination space, and an access position for placing the subject of interest in the examination space. The access position enables access to the examination space by moving away the radio frequency resonance device. The movement is a vertical movement which can be upwards or downwards, i.e. the radio frequency resonance device can be lowered to floor level or to an altitude, at which a patient can easily step over the radio frequency resonance device into the examination space. Preferably, the radio frequency resonance device is movable upwards, i.e. towards a ceiling of a room where the safety monitoring device is located. In case the room has a sufficient height, i.e. a height of at least the sum of the longitudinal extension of the examination space and the radio frequency resonance device, the ground of the location of the location of the safety monitoring device does has to be affected by the safety monitoring device.

According to a preferred embodiment the radio frequency resonance device comprises a first and a second tubular segment, whereby the segments are movable relative to each other between a closed position, in which the segments commonly enclose the examination space, and an open position, in which at least a segment of the radio frequency resonance device is removed for access. The segments refer to a part of the radio frequency resonance device, which extends preferably over the entire height of the radio frequency resonance device. Both segments together surround the entire examination space and accordingly cover an angle of 360 degrees. Preferably, the first segment covers an angle of at least 90 degrees. Further preferred, the each segment covers approximately an angle of 180 degrees of the radio frequency resonance device. Different kinds of movement of the two segments are possible to enable a patient to enter the examination space. One possibility is that one of the segments is fully removed from the other segment, so that it can be handled individually. Preferably, the two segments are connected to each other by at least one hinge joint, so that the first segment can be tilted relative to the other segment. Accordingly, the access can be provided in the way of a door access with the first segment moving like a door. Still further, both segments can be mounted to a support frame, and the first segment is mounted to the frame by means of at least one hinge joint, so that this segment is tiltable in respect to the frame. Hence, for accessing the examination space, the first segment is tilted from a vertical position towards a horizontal position, either upwards or downwards.

According to a preferred embodiment the extension of the examination space in the longitudinal direction is bigger than the extension of the radio frequency resonance device in the longitudinal direction, and the radio frequency resonance device is movable along the longitudinal axis. Hence, the corresponding method comprises moving the radio frequency resonance device along the longitudinal axis of the examination space. This provides a reliable scan over the entire length of the subject of interest located in the examination space covering also areas thereof, which are not of primary interest for the MR examination. E.g. when only a MR examination of the head is to be performed, the safety monitoring can cover the entire body to detect RF resonances by performing the movement along the longitudinal axis. Further preferred, the movement of the radio frequency resonance device in the longitudinal direction is longer than length of the subject of interest. In other words, the movement of the RF resonant structure is not limited directly by the dimensions of the subject of interest, but extends over the subject of interest so that at least half of the RF resonant structure extends over the longitudinal ends of the subject of interest. Accordingly, the safety monitoring device can comprise an elevated stand for the subject of interest or a stand that can be elevated, when the subject of interest has stepped on the stand. Hence, sitting provisions can be avoided and the movement of the RF resonant structure can be enabled to reliably cover the entire subject of interest.

Still further preferred, the movement along the longitudinal direction and the rotation of the radio frequency resonance device relative to the examination space are combined so that the radio frequency resonance device performs a helical or spiral movement in respect to the examination space. As described before, the rotation can be achieved by rotating either the radio frequency resonance device or the examination space. The distance of the spiral windings and the resulting number of turns of the radio frequency resonance device to cover the entire longitudinal extension of the examination space can be chosen according to accuracy requirements and a maximum duration of the safety monitoring for an efficient workflow prior to performing MR examinations.

According to a preferred embodiment the radio frequency resonance device is provided as a multi-resonant device comprising a single resonant structure, which covers at least two RF operation frequencies of different types of MR examination systems. Different MR examination systems have different operation frequencies depending on the field strength of the used magnetic field. For example, MR examination systems having field strength of 1.5 T and 3 T and have respective typical operation frequencies of 63-65 MHz and 126-129 MHz. Furthermore, operation frequencies can vary for different manufacturers resulting in variations of the operation frequency of typically several hundreds of kilohertz. This enables to deal with the multi-frequency issues, e.g. when one single safety monitoring device is used for monitoring safety for different types of MR examination systems. This implementation of the radio frequency resonance device can also be referred to as broadband implementation.

According to a preferred embodiment, the radio frequency resonance device is provided having at least two resonant structures, which are mutually decoupled, whereby each resonant structure covers the RF operation frequency of a different type of MR examination system. Different MR examination systems have different operation frequencies depending on the field strength of the used magnetic field. For example, MR examination systems having field strength of 1.5 T and 3 T have respective typical operation frequencies of 63-65 MHz and 126-129 MHz. Accordingly, a first resonant structure can be adapted for a MR examination system operating with a field strength of 1.5 T, and a second resonant structure can be adapted for a MR examination system operating with a field strength of 3 T. Furthermore, operation frequencies can vary for different manufacturers resulting in variations of the operation frequency of typically several hundreds of kilohertz. This enables to deal with the multi-frequency issues, e.g. when one safety monitoring device is used for monitoring safety for different types of MR examination systems. Preferably, the resonant structures are selected subsequently when monitoring RF resonances of the subject of interest. In case the radio frequency resonance device is moved in the longitudinal direction of the subject of interest for monitoring the RF resonances, preferably one resonant structure is selected when moving the RF resonance device in one direction and the other resonant structure is selected when moving the RF resonance device in the opposite direction. This implementation of the radio frequency resonance device can also be referred to as narrowband implementation.

According to a preferred embodiment the detection device is adaptable in its frequency for detecting the RF resonances of the subject of interest. In particular, the detection device can be set to a center frequency which corresponds with the frequency of the MR examination system. Accordingly, only a relatively narrow frequency band has to be monitored for RF resonances. Alternately, the detection device can cover multiple resonance frequencies of different MR examination systems, e.g. MR examination systems operating at different magnetic field strengths.

According to a preferred embodiment the safety monitoring device comprises a driving device, which is controllable by the controlling device, to drive at least one connection port of the radio frequency resonance device with low power. Hence, in the corresponding method, the step of monitoring an impedance of the at least one connection port of the radio frequency resonance device during the rotation comprises driving the at least one connection port of the radio frequency resonance device with low power. The driving device provides signals to at least one connection port of the radio frequency resonance device, preferably to all connection ports of the radio frequency resonance device. Preferably, the radio frequency resonance device has at least two connection ports, which are individually driven, e.g. with orthogonal RF signals. The driving device drives the connection ports to generate low power RF transmissions from the radio frequency resonance device. Low power refers to RF transmissions, which are significantly below the power of transmissions applied during MR examination, to avoid harm to the subject of interest. The driving device is preferably adapted to generate RF transmissions at an operation frequency of the MR examination system subsequently used for performing the MR examination. Known MR examination systems may have different operation frequencies depending on the manufacturer and the used strength of the static magnetic field. Typical values of the strength of the magnetic field are 1 T, 1.5 T, 3 T or 7 T. Further preferred, the generation of RF transmissions by the driving device can be adapted in frequency to cover the frequencies of different types of MR examination systems. Still further preferred, the detection device is adaptable in the selected frequency for detecting the RF resonances of the subject of interest. In particular, the detection device can be set to a center frequency which corresponds with the operation frequency of the MR examination system. Accordingly, only a relatively narrow frequency band has to be monitored for RF resonances.

According to a preferred embodiment the radio frequency resonance device comprises a transmission unit and a reception unit. Accordingly, the transmission unit can be driven for application of RF signals to the subjects of interest, and the reception unit receives the resonance signals from the subjects of interest. Hence, the transmission unit can be connected to a driving device and the reception unit can be connected to the detection device, which processes received RF signals to detect the radio frequency resonances. Further preferred, the transmission unit is provided as a coil, e.g. as a body coil, either as a birdcage coil or a TEM coil, and the reception unit is provided as at least one pick-up coil (PUC).

According to a preferred embodiment the safety monitoring device further comprises an alarming device, which is connected to the detection device. The alarming device can comprise a hardware alarm component, e.g. to generate an audible and/or a visual alarm in case the detection device detects a RF resonance within the subject of interest, and/or a software interface, e.g. for reporting the alarm to a control desk which is located apart from the safety monitoring device. The alarming device can comprise a graphical user interface to generate the alarm. The GUI can be adapted to provide additional information, e.g. in respect to the kind of alarm, the kind of resonance that caused the alarm, or a location of the monitored resonance.

BRIEF DESCRIPTION OF THE DRAWINGS

These and other aspects of the invention will be apparent from and elucidated with reference to the embodiments described hereinafter. Such an embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
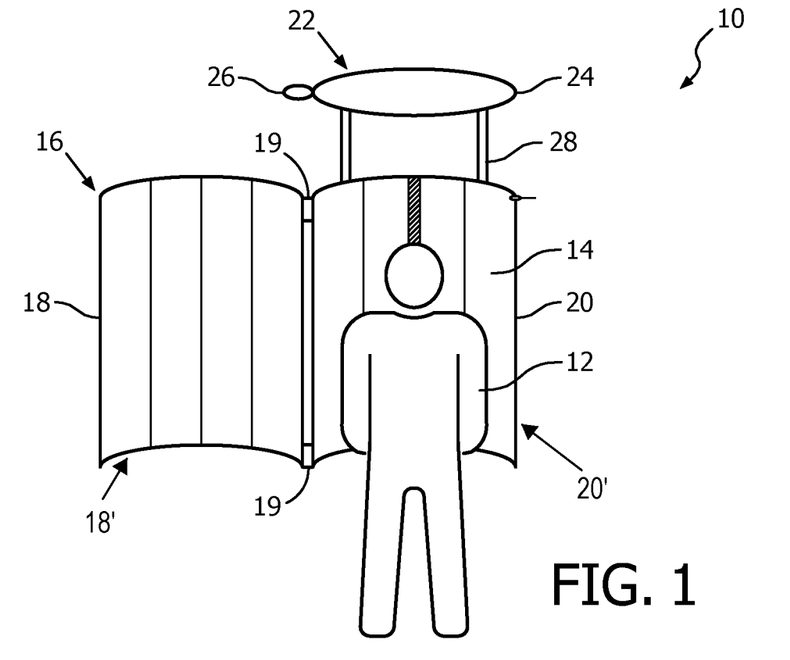
FIG. 1 is a frontal view of a schematic safety monitoring device according to a first embodiment in an open position with a subject of interest placed within its examination space.
Figure 2:
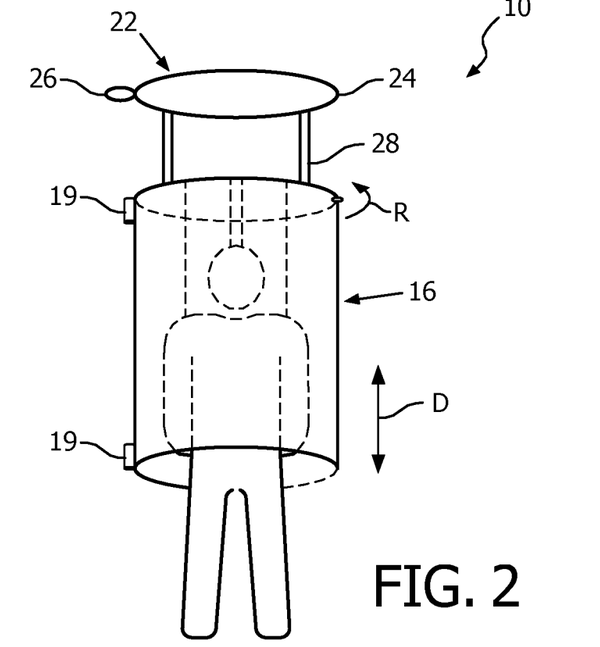
FIG. 2 is a frontal view of the schematic safety monitoring device according to the first embodiment in a closed position with a subject of interest placed within its examination space.

FIGS. 1 and 2 show a safety monitoring device 10 for detecting radio frequency (RF) resonances in a subject of interest 12, which is a human patient in this embodiment, according to a first, preferred embodiment. The safety monitoring device 10 is located outside a magnetic resonance (MR) examination room, where a MR examination system for subsequent MR examination is located.

The safety monitoring device 10 comprises an essentially tubular examination space 14, where the subject of interest 12 is to be located for detecting the radio frequency resonances. The examination space 14 is vertically arranged, i.e. the examination space 14 is positioned upright on a floor of a room, which is not shown, where the safety monitoring device 10 is located.

The safety monitoring device 10 further comprises a radio frequency (RF) resonance device 16, which is provided as a tubular coil in this embodiment, in particular as a birdcage coil. The RF resonance device 16 of the first embodiment is provided having two resonant structures 18, 20, which are mutually decoupled. Each resonant structure 18, 20 covers the RF operation frequency of a different type of MR examination system, e.g. the first resonant structure 18 covers typical operation frequencies of 63-65 MHz of a 1.5 T MR examination system, and the second resonant structure 20 covers typical operation frequencies of 126-129 MHz of a 3 T MR examination system.

The coil 16 has an essentially circular cross-section and a tubular shape and covers between 50-70 centimeter of the examination space 14 along its longitudinal axis. The RF resonance device 16 has a diameter in a closed position, which is shown in FIG. 2, of approximately 70 centimeter. The RF resonance device 16 comprises a first and a second tubular segments 18', 20', which coincide with the first and second resonant structures 18, 20. Both segments 18', 20' extend over the entire height of the RF resonance device 16 and each segment 18', 20' covers approximately an angle of 180 degrees of the RF resonance device 16. The two segments 18', 20' are connected to each other by two hinge joints 19, as shown in FIG. 1, so that the first segment 18' can be tilted towards the second segment 20'. Accordingly, the two segments 18', 20' can be tilted in the way of a door access with the first segment 18 moving like a door. The first segment 18' can be tilted between a closed position, in which the two segments 18' 20' commonly enclose the examination space 14, and an open position, in which the first segment 18' tilted away for access to the examination space 14. The RF resonance device 16 has two connection ports 21, which are RF/current contacts also serving as latches.

In an alternative embodiment, the RF resonance device 16 is provided as a volume TEM coil.

In a further alternative embodiment, the RF resonance device 16 is displaceable in the vertical direction between an operating position, in which the RF resonance device 16 is provided for covering at least a part of the examination space 14, and an access position for placing the subject of interest 12 in the examination space 14. The movement is a vertical movement which can be upwards or downwards, i.e. the RF resonance device 16 can be lowered to floor level or to an altitude, at which a patient can easily step over the RF resonance device 16 into the examination space 14. Alternatively, the RF resonance device 16 is movable upwards, i.e. towards a ceiling of a room where the safety monitoring device 10 is located, to enable access to the examination space 14.

The safety monitoring device 10 further comprises a rotation device 22, which is provided as a rotational support for the RF resonance device 16. The rotation device 22 is mounted e.g. on a ceiling of a room, where the safety monitoring device 10 is located, or on a support structure for supporting the rotation device 22. The rotation device 22 comprises a rotatable mounted ring element 24 and a motor 26 for rotating the ring element 24. The second segment 20 is mounted with support bars 28 to the ring element 24. The support bars 28 typically also provide mechanical access to the RF port connections 21. With the rotation device 22, the RF resonance device 16 is rotatable as indicated by the arrow R relative to the examination space 14 an accordingly relative to the subject of interest 12 when located in the examination space 14.

In an alternative embodiment, the rotation device 22 is provided as a rotational stand for the subject of interest 12. Accordingly, the relative rotation between the examination space with the subject of interest 12 and the RF resonance device 16 is achieved by a mere rotation of the stand.

The RF resonance device 16 is adapted to perform a longitudinal movement along the arrow D. Accordingly, the RF resonance device 16 is movable along the longitudinal axis along the entire examination space 14. The safety monitoring device is adapted to perform the movement of the RF resonance device 16 between a lower position, where at least half of the RF resonance device 16 is located below the examination space, and an upper position, where at least half of the RF resonance device 16 is located above the examination space In operation, i.e. when monitoring RF resonances in the subject of interest 12, the movement along the arrow D and the rotation along the arrow R are combined to form a helical or spiral movement in respect to the examination space 14. The distance of the spiral windings and the resulting number of turns of the RF resonance device 16 to cover the entire longitudinal extension of the examination space 14 are chosen according to accuracy requirements and a maximum duration of the safety monitoring.

Figure 4:
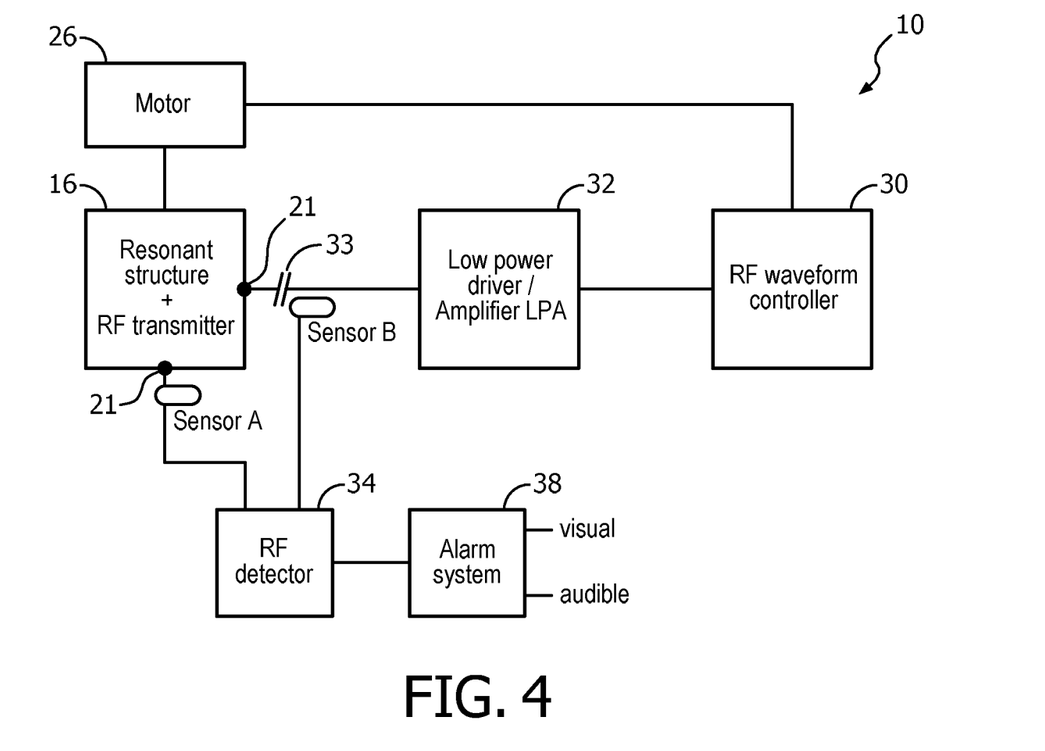
FIG. 4 is a block diagram of an RF part of the safety monitoring devices of the first and second embodiment.

The safety monitoring device 10 further comprises a controlling device 30 for controlling the rotation of the RF resonance device 16, as shown in FIG. 4. The controlling device 30 is also adapted for controlling the movement of the RF resonance device 16 along the arrow D.

The safety monitoring device 10 also comprises a driving device 32, which is a low power amplifier in this embodiment. The driving device 32 is controllable by the controlling device 30 to drive the two connection ports 21 of the RF resonance device 16 individually. The driving device 32 provides driving signals to the connection port 21 via sliding contacts 33, from which only one is shown, to drive the generation of low power RF signals from the coil 16. Low power RF signals refer to RF transmissions which are significantly below transmissions power applied during MR examination to avoid harm to the subject of interest 12. The controlling device 30 and the driving device 32 are adapted to generate RF transmissions at an operation frequency of MR examination systems subsequently used for performing MR examination, which are a 1.5 T and 3 T MR examination systems. The controlling device 30 and the driving device 32 are adapted to provide signals with a frequency of still different types of MR examination systems.

With respect to FIG. 4, the safety monitoring device 10 further comprises a detection device 34 for detecting radio frequency resonances. Accordingly, the detection device 34 is connected with two sensors 36, which are located in proximity of the connection ports 21 of the coil 16. The sensors 36 in this embodiment are directional couplers for sensing reflected power at the connection ports 21. The detection device 34 is adapted to receive the reflected power at the connection ports 21 and to calculate and monitor an impedance of the connection ports 21 of the RF resonance device 16 during a rotation of the RF resonance device 16. Accordingly, the detection device 34 is set to a center frequency which corresponds with the frequency of the 3 T MR examination system in this embodiment system and is adapted to detection of the RF resonances in a relatively narrow frequency band around the center frequency. The detection device 34 is adapted to receive signals with a frequency of the 1.5 T and 3 T MR examination systems, as specified above, and to modify its center frequency respectively. The detection device 34 is adapted to detect RF resonances out of the monitored impedance by comparing the monitored impedance to a table of impedance values different subjects of interest 12 which comprise no elements which cause RF resonances. The table of impedance values comprises reference values for different kinds of subjects of interest depending on their typical responses, i.e. reference patient having a different height, weight and/or characteristic anatomy. The reference patient is selected by an operator using a graphical user interface of the safety monitoring device 10.

In an alternative embodiment, detection device 34 is provided as a broadband implementation for coverage of a frequency range of both MR examination systems, i.e. MR examination systems having static magnetic fields of 1.5 T and 3 T.

The safety monitoring device 10 further comprises an alarming device 38, which is connected to the detection device 34. The alarming device 38 is provided to generate an audible and a visual alarm in case the detection device 34 detects a RF resonance within the subject of interest.

Figure 5:
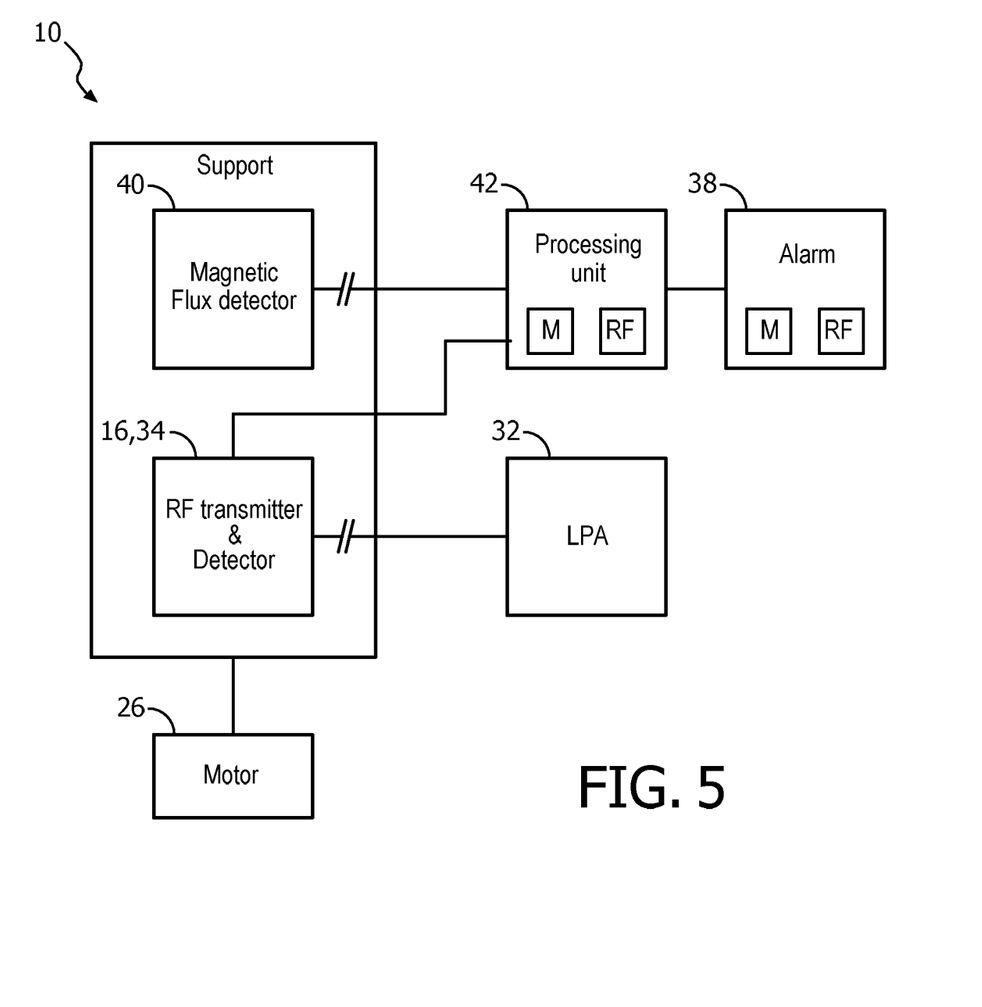
FIG. 5 is a block diagram of the safety monitoring devices of the first and second embodiment additionally covering its ferromagnetic detection device.

The safety monitoring device 10 further comprises a ferromagnetic detection device 40 to detect the presence of ferromagnetic objects within the examination space 14. The ferromagnetic detection device 40 is mounted to the RF resonance device 16, i.e. the ferromagnetic detection device 40 is attached to the coil 16, in particular to the second tubular segment 20. Accordingly, the ferromagnetic detection device 40 is movable together with the RF resonance device 16.

As shown with respect to FIG. 5, the safety monitoring device 10 comprises a processing device 42 for processing signal indicating a RF resonance in the subject of interest 12, which is provided from the detection device 34, and signals indicating a ferromagnetic object in the subject of interest 12, which is provided from the ferromagnetic detection device 40. The alarming device 38 is connected to the processing device 42, so that a single alarming device 38 can be used to generate an alarm in case of a RF resonance or a ferromagnetic object in the subject of interest 12.

The operation of the safety monitoring device 10 is as follows. The RF resonance device 16 is provided in its open position to enable access of the subject of interest, which is vertically located in the examination space 14. After tilting the tubular segment 18' into its closed position, the two tubular segments 18', 20' form the tubular coil 16 for monitoring the RF resonances. Monitoring starts with the RF resonance device 16 in its upper position. The safety monitoring device 10 is set to the operation frequency of the 1.5T MR examination system, i.e. the driving device 32 and the detection device 34 are set to the respective frequency and the first resonant structure 18' is selected to be driven.

When monitoring starts, the RF resonance device 16 is rotated by the rotation device 22 along arrow R and additionally moved downwards along the arrow D to perform a helical movement around the examination space 14. During this movement, the connection port 21 of the first resonance structure of the RF resonance device 16 is driven by driving device 32, and the impedance of the RF resonance device 16 at the connection port 21 of the first resonant structure 18 is monitored by the detection device 34. Accordingly, the connection port 21 of the first resonance structure 18 is switched using sliding contacts 33 between driving operation where the connection port 21 is connected to the driving device 32, and monitoring operation, where the connection port 21 is connected to the detection device 34. The detection device 34 monitors the impedance of the first resonant structure 18 and compares the impedances to the values of the reference patient to identify RF resonances. Accordingly, the detection device 34 compares the monitored impedances to a calibrated response for the subject of interest 12. In parallel, the ferromagnetic detection device 40 monitors the examination space 14 for ferromagnetic elements.

When the RF resonance device 16 has reached its lower position, the safety monitoring device 10 is set to the operation frequency of the 3 T MR examination system, i.e. the driving device 32 and the detection device 34 are set to the respective frequency and the second resonant structure 18 is selected to be driven. Then, the RF resonance device 16 is moved upwards along the arrow D to the upper position together with the rotation by the rotation device 22 along arrow R to perform again a helical movement around the examination space 14. During this movement, the connection port 21 of the first resonance structure of the RF resonance device 16 is driven by driving device 32, and the impedance of the RF resonance device 16 at the connection port 21 of the second resonant structure 20 is monitored by the detection device 34. Accordingly, the connection port 21 of the first resonance structure 18 is switched using sliding contacts 33 between driving operation where the connection port 21 is connected to the driving device 32, and monitoring operation, where the connection port 21 is connected to the detection device 34. The detection device 34 monitors the impedance of the first resonant structure 18 and compares the impedances to the values of the reference patient to identify RF resonances as described above. In parallel, the ferromagnetic detection device 40 still monitors the examination space 14 for ferromagnetic elements.

When the resonance device 16 has reached the upper position, monitoring is finished. The RF resonance device 16 is again provided in its open position to enable the subject of interest to leave the examination space 14.

In case a ferromagnetic element or a RF resonance is discovered, this is reported to the processing device 42, which generates an alarm using the alarming device 38. When the operation of the safety monitoring device 10 is stopped, the RF resonance device 16 is again provided in its open position, so that subject of interest 12 can exit the examination space 14.

Figure 3:
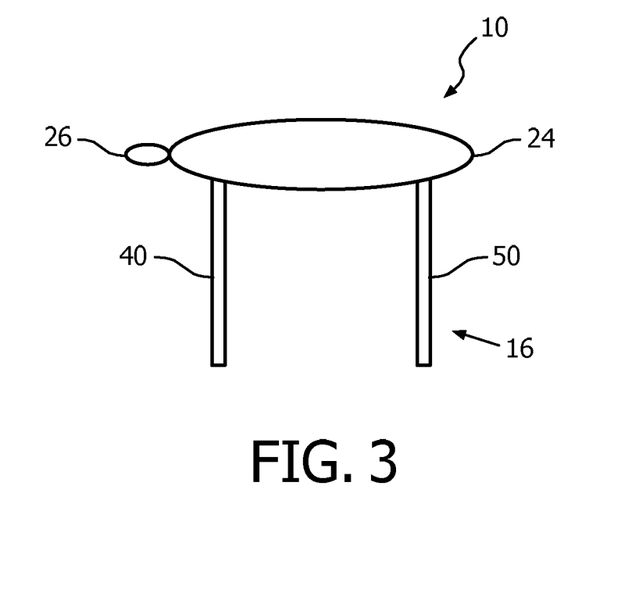
FIG. 3 is a frontal view of a schematic safety monitoring device according to a second embodiment.

FIG. 3 refers to a second embodiment of the safety monitoring device 10. The second embodiment differs from the above described first embodiment in the RF resonance device 16.

According to the second embodiment the RF resonance device 16 is provided with one single element resonant structure 50. The single element resonant structure 50 in this embodiment is a TEM element, which is supported at ring 24 of the rotation device 22 as described in respect to the first embodiment. The single element resonant structure 50 has the shape of a bar extending in a vertical direction. As further difference, the ferromagnetic detection device 40 is mounted directly to the ring 24. The single element resonant structure 50 is provided as a multi-resonant device, which covers the RF operation frequencies of different types of MR examination systems, i.e. operation frequencies of the 1.5 T and 3 T MR operation system as described above. The single element resonant structure 50 has a connection port 21, which is connected as described above to the driving device 32. With the single element resonant structure 50, access the examination space is granted without movement of the RF resonance device 16.

The further components and the usage of the safety monitoring device 10 according to the second embodiment is as described before in respect to the first embodiment. With the RF resonance device 16 having only one single element resonant structure 50, the single element resonant structure 50 is driven both during the movement upwards and downwards, and shifting of the resonant structures 18, 20 of the first embodiment is omitted.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

REFERENCE SYMBOL LIST 10 safety monitoring device
12 subject of interest
14 examination space
16 radio frequency (RF) resonance device, coil
18, 18' first resonant structure, first tubular segment
19 hinge joint
20, 20' second resonant structure, second tubular segment
21 connection port
22 rotation device
24 ring element
26 motor
28 support bar
30 controlling device
32 driving device, low power amplifier
33 sliding contacts
34 detection device
36 sensor
38 alarming device
40 ferromagnetic detection device
42 processing device
=single element resonant structure
R arrow, rotation
D arrow, movement

The invention claimed is:

1. A safety monitoring device for detecting radio frequency resonances in a subject of interest prior to a magnetic resonance examination, the safety monitoring device comprising:
an essentially tubular examination space, for locating therein the subject of interest;
a radio frequency resonance device comprising at least one connection port and a tubular coil covering at least a part of the essentially tubular examination space, and being movable along a longitudinal axis of the essentially tubular examination space;
a rotation device for rotating the radio frequency resonance device relative to the essentially tubular examination space;
a controlling device for controlling the rotation of the radio frequency resonance device; and
a detection device for detecting radio frequency resonances by monitoring an impedance of the at least one connection port of the radio frequency resonance device during the rotation, the radio frequency resonances indicating presence of radio frequency resonant structure in the subject of interest.

2. The safety monitoring device according to claim 1, wherein the radio frequency resonance device has a plurality connection ports and the detection device comprises sensors at the respective connection ports for sensing reflected power at the connection ports.

3. The safety monitoring device according to claim 1, further comprising a ferromagnetic detection device to detect a presence of ferromagnetic objects in the subject of interest, as the detection device is detecting the radio frequency resonances.

4. The safety monitoring device according to claim 1, wherein the rotation device is a rotational stand for the subject of interest.

5. The safety monitoring device according to claim 1, wherein the rotation device is provided as a rotational support for the radio frequency resonance device.

6. The safety monitoring device according to claim 1, wherein the tubular coil substantially covers the examination space along its longitudinal axis.

7. The safety monitoring device according to claim 1, wherein the radio frequency resonance device is provided as a multi-resonant device comprising a single resonant structure, which covers at least two RF operation frequencies of different types of MR examination system.

8. The safety monitoring device according to claim 1, wherein the radio frequency resonance device is movable along the longitudinal axis between an operating position, in which the radio frequency resonance device is provided for covering at least a part of the examination space, and an access position for placing the subject of interest in the examination space.

9. The safety monitoring device according to claim 1, wherein the radio frequency resonance device comprises a first and a second tubular segment, whereby the segments are movable relative to each other between a closed position, in which the segments commonly enclose the examination space, and an open position, in which at least one segment of the radio frequency resonance device is removed for access.

10. The safety monitoring device according to claim 1, wherein the safety monitoring device comprises a driving device, which is controllable by the controlling device, to drive at least one connection port of the radio frequency resonance device with low power.

11. A method for detecting radio frequency resonances in a subject of interest, the method comprising:
locating the subject of interest within an essentially tubular examination space;
rotating a radio frequency resonance device comprising at least two resonant segments, which are mutually decoupled, whereby each resonant structure covers an RF operation frequency of a different type of MR examination system, the radio frequency resonance device further comprising at least one connection port relative to at least a part of the examination space along its longitudinal axis;
monitoring an impedance of the at least one connection port of the radio frequency resonance device during the rotation;
detecting radio frequency resonances out of the monitored impedance of the at least one connection port of the radio frequency resonance device prior to a magnetic resonance examination of the subject of interest; and determining that a radio frequency resonant structure is in the subject of interest when the radio frequency resonances are detected.

12. The method according to claim 11, comprising moving the radio frequency resonance device along the longitudinal axis of the examination space.

13. The method according to claim 11, wherein the monitoring the impedance of the at least one connection port of the radio frequency resonance device during the rotation comprises driving the at least one connection port with low power.

14. A safety monitoring device for detecting radio frequency resonances in a subject of interest prior to a magnetic resonance examination, the safety monitoring device comprising:

an essentially tubular examination space, for locating therein the subject of interest;

a radio frequency (RF) resonance device comprising at least two resonant segments, which are mutually decoupled, whereby each resonant structure covers an RF operation frequency of a different type of MR examination system, the radio resonance device further comprising at least one connection port covering at least a part of the examination space along a longitudinal axis, wherein the RF resonance device is displaceable along the longitudinal axis;

a rotation device for rotating the radio frequency resonance device relative to essentially tubular examination space while the RF resonance device is displaced along the longitudinal axis;

a controlling device for controlling the rotation of the radio frequency resonance device; and a detection device for monitoring an impedance of the at least one connection port of the radio frequency resonance device during the rotation and detecting radio frequency resonances out of the monitored impedance of the at least one connection port of the radio frequency resonance device.

15. The safety monitoring device according to claim 14, wherein the at least two segments are adapted to be tilted away from each other, and towards each other.

16. The safety monitoring device according to claim 15, wherein when the at least two segments are tilted away from each other, access to the examination space is provided.

17. The safety monitoring device according to claim 14, wherein when the at least two segments are tilted towards from each other no access to the examination space is provided.

18. The safety monitoring device as claimed in claim 14, wherein the at least one connection port is a first connection port, and the RF resonance device further comprises a second connection ports, wherein the first and second connection ports are latches between the at least two resonant segments.

19. The safety monitoring device as claimed in claim 14, wherein the at least two resonant segments are connected to each other by hinge joints.

20. The method according to claim 11, wherein detecting radio frequency resonances out of the monitored impedance comprises comparing the monitored impedance to a table of impedance values of different subjects of interest that include no radio frequency resonant structure.

* * * * *